United States Patent [19]

Siezen et al.

[11] Patent Number: 4,665,089

[45] Date of Patent: May 12, 1987

[54] PROCESS FOR PREVENTING OR REVERSING CATARACT FORMATION USING PROTEIN MODIFICATION REAGENTS

[75] Inventors: Roelant J. Siezen, Arlington, Mass.; Christophe M. Coppin, Simsbury, Conn.; George B. Benedek, Belmont, Mass.

[73] Assignee: Massachusetts Institute of Technology, Cambridge, Mass.

[21] Appl. No.: 714,599

[22] Filed: Mar. 21, 1985

[51] Int. Cl.4 .................... A61K 31/40; A61K 31/215
[52] U.S. Cl. .................................... 514/422; 514/425; 514/508; 514/912
[58] Field of Search ................ 514/422, 425, 508, 912

[56] References Cited

U.S. PATENT DOCUMENTS

| | | | |
|---|---|---|---|
| 4,150,120 | 4/1979 | Ono ...................................... | 514/912 |
| 4,351,826 | 9/1982 | Clark .................................... | 424/81 |
| 4,451,477 | 5/1984 | Silvestrini et al. ................... | 514/912 |
| 4,474,817 | 10/1984 | Clark .................................... | 424/333 |

OTHER PUBLICATIONS

Chem. Abst. 81:1550p (1974)–Raubach et al.
Chem. Abst. 97:141268h (1982)–Nemes et al.

*Primary Examiner*—Douglas W. Robinson
*Attorney, Agent, or Firm*—Paul J. Cook

[57] ABSTRACT

Cataract in mammalian lenses can be prevented or reversed by applying a solution of an imidoester, a N-hydroxysuccinimide-ester or hydrogen peroxide to the lens under conditions that permit the solution to interact with the lens constituents.

12 Claims, No Drawings

PROCESS FOR PREVENTING OR REVERSING CATARACT FORMATION USING PROTEIN MODIFICATION REAGENTS

BACKGROUND OF THE INVENTION

The Government has rights in this invention under Grant Numbers NIH-7-R01-EY05127-02 and NIH-1-R01-EY05496-01 from the National Institutes of Health.

This invention relates to a process for preventing or reversing cataract formation in the lens of the eye.

Cataract disease is a worldwide medical problem causing blindness in over 1.25 million people annually. Cataracts generally are caused by structural inhomogeneities within lens tissue which become large enough to scatter light and reduce the normal transparency of the lens. The primary treatment for cataract is surgery and the surgical technique utilized comprises excising the cataractous lens and, in some cases, replacing it with a plastic implant. This operation is delicate, expensive and is usually performed on elderly individuals. At the present time, there is no effective nonsurgical treatment for cataracts either by way of prevention or reversal of the light scattering in order to avoid the inherent danger and expense associated with surgical techniques for removing cataracts.

Prior to this invention, it has been disclosed in U.S. Pat. Nos. 4,351,826 and 4,474,817 to utilize glycols, acrylamides and/or aldehydes to prevent or reverse cataract formation. However, it has been found that treatment with most of these reagents is reversible. Accordingly, it would be desirable to provide reagents which prevent or reverse cataract formation substantially irreversibly.

SUMMARY OF THE INVENTION

The present invention is based on the discovery that certain classes of chemical reagents have the effect of inhibiting or reversing the formation of cataracts when administered to eye lenses. The reagents are imido-esters, N-hydroxysuccinimide-esters (NHS-esters) and hydrogen peroxide. They appear to interact with the protein constituents of the lens to prevent their association and to stabilize them against subsequent aggregation. An aqueous solution of the reagent which is physiologically acceptable to the eye is administered directly to the lens in a manner such that the solution penetrates the lens structure throughout its thickness for a period of time sufficient to permit interaction of the treating reagent with the proteins in the lens.

An advantage of these reagents over the previously patented glycols and acrylamides (U.S. Pat. Nos. 4,351,826 and 4,474,817) is that the prevention of cataract formation by imidoesters, NHS-esters and hydrogen peroxide is generally permanent. In addition, considerably lower reagent concentrations are effective than those needed in treatment with glycols, aldehydes and acrylamides.

DETAILED DESCRIPTION OF SPECIFIC EMBODIMENTS

In accordance with this invention, the lens of the eye is treated with a solution containing a chemical reagent which interacts with the protein molecules in the lens cytoplasm. The solution is applied to the lens for a period of time and under conditions such that the reagent which interacts with the protein molecules permeates the entire lens. The solution can be applied in any convenient manner such as with an eye dropper, microinjection, lysosomes, implanted timed release capsule or soaking apparatus. Generally, application of the treating solution is effected over a period of between 24 and 94 hours (1 to 4 days), under normal room temperature condition, but may be shorter. The chemical reagents utilized in this treatment prevent or reverse the aggregation of the protein molecules so as to eliminate light scattering and relieve the symptoms of cataract.

The imido-esters and NHS-esters are believed to react primarily with the amino groups of a protein molecule, thereby forming a covalent link between the protein molecule and part of the reagent. The reagent is thereby split at its ester bond. When utilizing imidoesters the byproduct will be an alcohol, such as methanol or ethanol; utilizing NHS-esters the byproduct is N-hydroxysuccinimide (NHS).

Imidoester reaction with protein

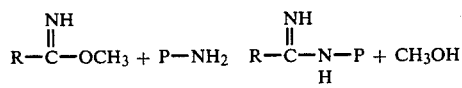

NHS-ester reaction with protein

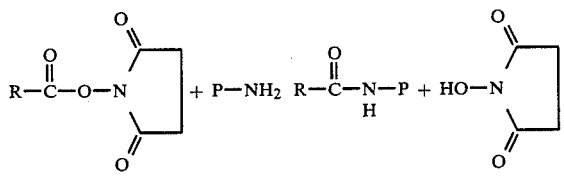

wherein P=protein molecule, R=remainder of reagent molecule, such as alkyl, thioalkyl, alkylamido, hydroxyalkyl, etc.

Bifunctional imido-esters and NHS-esters have two reactive groups, which can react with two different protein amino groups, whereas monofunctional reagents react with only one protein amino group. When bifunctional reagents react with two amino groups on different protein molecules, a covalent crosslink is formed between these protein molecules. Since proteins contain many amino groups, it is possible, in principle, to generate a chain link or stabilized three-dimensional network of protein molecules within the lens. Monofunctional reagents will not crosslink protein molecules, since they only modify a single protein amino group per reagent molecule. In addition, bifunctional reagents will not form a crosslink between different protein molecules if the two reactive groups on either end of the reagent molecule react with two amino groups on the same protein molecule; this type of reaction leads to an internal crosslink in a single protein molecule. Likewise, no crosslink will be formed at all if one (or both) reactive groups of the reagent are hydrolyzed prior to reaction with an amino group.

General structure of a bifunctional imido-ester

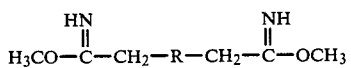

General structure of a bifunctional NHS-ester

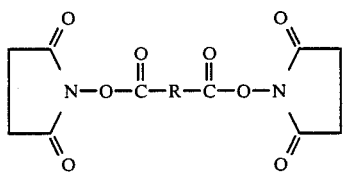

wherein R = remainder of the reagent molecule, which can be varied to change reagent length, reagent hydrophobicity/hydrophilicity, introduce additional labile bonds, etc.

In general, the modification of protein molecules with imido-esters and NHS-esters is irreversible, since the newly formed covalent bonds are not cleavable under physiological conditions of pH, temperature, etc. Hence, any effects these reagents have in preventing cataract formation or reversing existing cataracts in the lens should also be irreversible. Some bifunctional reagents have an additional internal labile covalent bond which can be cleaved under physiological conditions by adding a suitable cleaving reagent. If the labile bond is a disulfide (—S—S—), cleavage of this bond can be induced by the addition of a reducing agent such as mercaptoethanol (MSH), dithiothreitol (DTT) or glutathione (GSH). Therefore, a crosslink formed between two protein molecules, utilizing a bifunctional reagent with internal labile bond can be subsequently broken with a suitable cleavage reagent, thereby separating the two protein molecules. In this fashion it can be established whether the prevention or reversal of cataract utilizing bifunctional reagents is due to either protein amino group modification, protein crosslinking or both.

Representative monofunctional imido-esters suitable for cataract inhibition or reversal are shown in Table 1 and include methylacetimidate (MA), ethylacetimidate (EA) and methyl-3-thio propionimidate (MTP); suitable bifunctional imidoesters include dimethyladipimidate (DMA), dimethylsuberimidate (DMS) and dimethyl-3,3'-dithiobispropionimidate (DTBP). An exemplary monofunctional NHS-ester is thiosuccinimidyl propionate (TSP); suitable bifunctional NHS-esters disuccinimidyl tartrate (DST), disuccinimidyl suberate (DSS), dithiobissuccinimidyl propionate (DTSP) and ethylene glycolbis(succinimidyl succinate) (EGS). In addition, it is to be understood that each of the reagents suitable for use herein may also be used in a mixture with one or more of any of the other suitable reagents.

TABLE 1

Imido-esters monofunctional

MA    $CH_3-\underset{\underset{NH}{\|}}{C}-OCH_3$

EA    $CH_3-\underset{\underset{NH}{\|}}{C}-OCH_2-CH_3$

MTP    $HS-CH_2-CH_2-\underset{\underset{NH}{\|}}{C}-OCH_3$ bifunctional

DMA    $H_3CO-\underset{\underset{NH}{\|}}{C}-CH_2-CH_2-CH_2-CH_2-\underset{\underset{NH}{\|}}{C}-OCH_3$ DMS    $H_3CO-\underset{\underset{NH}{\|}}{C}-CH_2-CH_2-CH_2-CH_2-CH_2-CH_2-\underset{\underset{NH}{\|}}{C}-OCH_3$ DTBP    $H_3CO-\underset{\underset{NH}{\|}}{C}-CH_2-CH_2-S-S-CH_2-CH_2-\underset{\underset{NH}{\|}}{C}-OCH_3$ NHS—esters monofunctional TSP    $HS-CH_2-CH_2-\underset{\underset{O}{\|}}{C}-O-N\text{(succinimidyl)}$ bifunctional DTSP    (succinimidyl)$N-O-\underset{\underset{O}{\|}}{C}-CH_2-CH_2-S-S-CH_2-CH_2-\underset{\underset{O}{\|}}{C}-O-N$(succinimidyl)

TABLE 1-continued

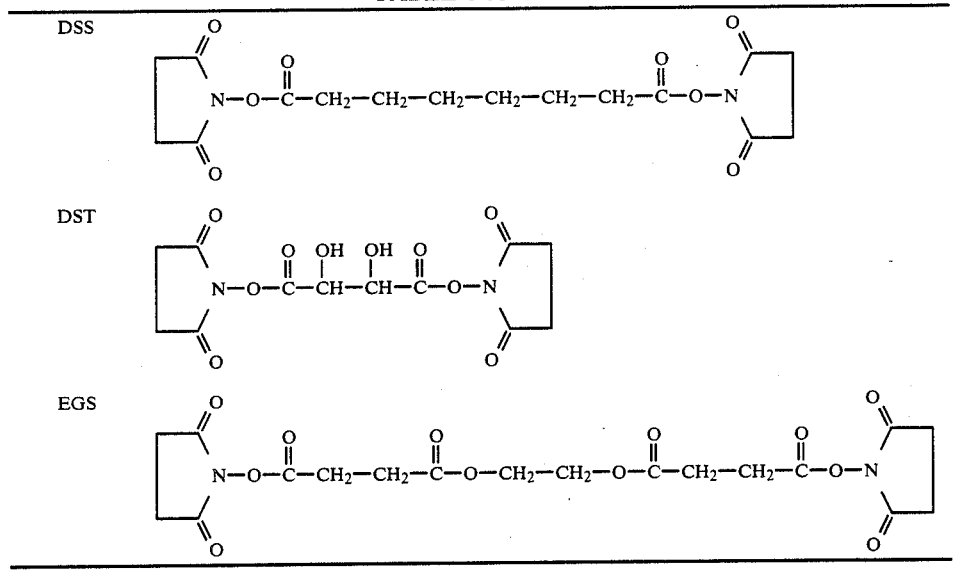

Hydrogen peroxide ($H_2O_2$) is a general oxidizing agent. Its modifying effect on proteins is to oxidize the side chain of certain amino acid residues, primarily cysteine, methionine and tryptophan. Methionine is oxidized to methionine sulfoxide and ultimately methionine sulfone, whereas cysteine is oxidized to cystine and cysteic acid. These oxidation reactions are not readily reversible under physiological conditions by simple reduction with a reducing agent, with one exception. Formation of cystine involves the oxidation of two adjacent cysteine residues, thereby creating a disulfide bond (—S—S—) crosslink. Crosslinking can occur within a single protein molecule (intra-molecular) or between two different protein molecules (inter-molecular). In either case, the disulfide bond crosslink can be readily broken under physiological conditions by the addition of a reducing agent, such as MSH, DTT or GSH. Again, this is a simple way of testing whether the prevention of cataract formation by hydrogen peroxide is due to protein modification, crosslinking or both.

The effective concentration and composition of the solution utilized in treatment will depend on the specific requirement that the solution be physiologically acceptable to the eye. The imido-esters, NHS-esters and hydrogen peroxide are utilized in solutions of 0.005 to about 0.050 molar concentration. The carrier solutions are aqueous and can be buffered with a physiologically acceptable salt such as a phosphate in order to adjust the pH of the solution to approximately that of the lens, which is about 7.0. In the case of NHS-esters, a small amount of organic solvent such as dimethylsulfoxide (DMSO) or dimethylformamide (DMF) is required initially to dissolve these modification agents, since they are poorly soluble in aqueous solutions.

To test each compound, the lenses can be removed from the eye and placed in solutions of the desired chemical reagent. When so tested, it has been found that hydrogen peroxide will reverse opacification in cataracts induced in calf lens nucleus by low temperature, so-called cold cataract. The induction of cold cataracts in calf lenses can be prevented when the transparent lenses are treated with imido-esters, NHS-esters or hydrogen peroxide.

While the applicants do not intend to be limited to a specific theory regarding the mechanism of this invention, it is believed that the reagents in the present invention are involved primarily in chemical modification of side chain groups (such as amino groups, sulfhydryl groups) of protein molecules within the lens. In addition, some of the described reagents could be involved in chemical crosslinking of protein molecules within the lens. Treatment of isolated calf lenses with a solution containing hydrogen peroxide as described, increased the hardness of the lens and increased the amount of high molecular weight protein aggregates which could be extracted from the lens. These changes are characteristic of crosslinking reactions between protein molecules. Most of the crosslinks were found to be cystine disulfide bonds, since the high molecular weight protein aggregation could be reversed by treatment of the isolated aggregates with a reducing agent. This cleavage of crosslinks did not reverse the effects hydrogen peroxide treatment has in preventing lens opacification. This implies that protein modification itself, by hydrogen peroxide, rather than the subsequent crosslink formation may be primarily responsible for prevention of cataract.

This theory is substantiated by the tests performed on calf lenses with solutions of imido-esters and NHS-esters. Both mono-functional and bi-functional reagents were effective in preventing cataract formation of the lens nucleus. This prevention of opacification could not be reversed by placing the treated lenses back in saline solution without reagent, nor could it be reversed by cleaving the bifunctional reagents which had an internal labile disulfide bond. In fact, very little intermolecular protein crosslinking was evident utilizing bifunctional imido-esters and NHS-esters. The treated lenses remained soft, clear and colorless, and no increase of high molecular weight protein aggregates occurred. These results suggest that modification of protein amino groups without subsequent crosslinking is the mechanism by which both imido-esters and NHS-esters prevent opacification of the eye lens under physiological reaction conditions. Protein modification changes the surface characteristics of the proteins and thereby their ability to interact with each other and form larger aggregates. Treatment of calf lenses with the modifying agents described presumably modifies the surface of lens proteins such that they are less inclined to interact and form high molecular weight aggregates which scatter light excessively.

The following example illustrates the present invention and is not intended to limit the scope of this invention.

EXAMPLE I

This example illustrates that imido-esters, NHS-esters and hydrogen peroxide can be utilized to prevent and reverse opacification of eye lenses.

Solutions of 0.005 to 0.050 molar concentration of hydrogen peroxide, DTBP, DSP, DST, DSS and EGS (see Table I for nomenclature) were made up in 0.1M phosphate buffered saline of pH=7.0, ionic strength 0.22. This salt concentration and pH are very similar to those found in the intact lens. Monofunctional reagents were prepared from solutions of DTBP and DSP by adding equimolar concentrations of the reducing agent mercaptoethanol (MSH) or dithiothreitol (DTT). Freshly excised calf lenses were placed in 5 ml of each solution in a sealed vial and soaked for 24 to 96 hours at room temperature. At least 24 hours appears to be required to allow the reagent to diffuse throughout the entire lens. The transparency of each lens was then measured as a function of decreasing temperature with a laser beam focused at the center of the lens. At a certain temperature the lens begins to opacify due to increased light scattering. The opacification temperature is defined as the temperature at which lens transmittance decreases to 90% of its normal transparent value.

The nucleus of an untreated calf lens opacifies when the temperature of the lens decreases below 13° C., on average (some variation is attributable to age differences). The treated lenses opacified at a lower temperature, and representative values are summarized in Table II.

In general, opacification temperatures were found to decrease progressively with increasing time of treatment or increasing reagent concentration. Both mono- and bi-functional reagents were effective. Reducing agents alone, such as MSH, DTT or GSH, had no effect. It should be noted that imidoesters have a high pH optimum of reaction with amino groups, namely pH 9–10, and the imidoesters are actually rather unstable and susceptible to hydrolysis at physiological pH 7. A higher reaction rate, degree of crosslinking and perhaps effectiveness in preventing cataract may be achieved, therefore, if experimental conditions can be adapted to treat lenses at higher pH with solutions of imido-esters. While all of the described reagents are effective in preventing opacification of the lens nucleus, they tend to reduce the clarity of the lens periphery when used in excess of 0.05 molar concentration. Low concentrations of hydrogen peroxide have a similar effect on the lens, but this can be avoided by pretreatment with reducing agent.

TABLE II

| Reagent | Reagent Concentration (mM) | Incubation Time (Hrs) | Opacification Temperature (°C.) |
|---|---|---|---|
| none |  |  | 13° |
| IMIDO-ESTERS | | | |
| monofunctional DTBP + DTT | 30 | 24 | 2° |
| bifunctional DTBP | 30 | 72 | 5° |
| NHS-ESTERS | | | |
| monofunctional DTSP + MSH | 20 | 96 | 4° |
| bifunctional | | | |
| DTSP | 30 | 96 | 5° |
| DST | 40 | 24 | 3° |
| DSS | 30 | 24 | 1° |
| EGS | 40 | 72 | 0° |
| OXIDIZING AGENTS | | | |
| hydrogen peroxide | 30 | 24 | 0° |

From Table II it is evident that 0.02 to 0.04 molar concentration of these reagents lower the opacification temperature of the lens nucleus by 8° C. or more, or in other words, lens transparency is maintained down to 5° C. or less. When the lenses are returned to 0.1M phosphate buffered saline without modification reagent, and the excess reagent is allowed to diffuse out of the lens, it was found that 60–70% of the initially observed depression of the opacification temperature remained. In other words, the effect of these reagents is permanent in the sense that even after removal of reagent, normal transparency of the treated lens is maintained at temperatures considerably lower than 13° C., the temperature at which the untreated lens opacifies.

In another experiment, it was demonstrated that hydrogen peroxide can improve the transparency of opacified eye lenses. A fresh calf lens was first cooled in 5 ml saline solution to 5° C., a temperature at which the lens nucleus is completely opaque. Hydrogen peroxide at 0.05 molar concentration was subsequently added. After soaking in hydrogen peroxide solution for 72 hours, the lens nucleus reversed to normal transparency, at 5° C.

We claim:

1. A method of preventing or reversing cataract formation in the lens of the eye which comprises:
   administering a therapeutically effective amount of a physiologically acceptable solution of a reagent to the lens, said reagent being selected from the group consisting of an imido-ester having the formula

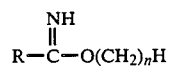

wherein R represents the remainder of the reagent molecule and n is at least 1,
an N-hydroxy-succinimide ester having the formula

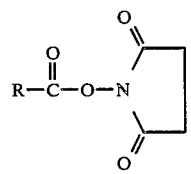

wherein R represents the remainder of the reagent molecule, and a mixture thereof.

2. The method of claim 1 wherein the reagent is an imido-ester.

3. The method of claim 1 wherein the reagent is an N-hydroxy-succinimide ester.

4. The method of claim 2 wherein the imido-ester comprises methyl-acetimidate.

5. The method of claim 2 wherein the imido-ester comprises ethyl-acetimidate.

6. The method of claim 2 wherein the imido-ester comprises dimethyl-adipimidate.

7. The method of claim 2 wherein the imido-ester comprises dimethyl-suberimidate.

8. The method of claim 2 wherein the imido-ester comprises dimethyl-3,3'-dithiobispropionimidate.

9. The method of claim 3 wherein the reagent is dithiobissuccinimidyl propionate.

10. The methiod of claim 3 wherein the reagent is disuccinimidyl tartrate.

11. The method of claim 3 wherein the reagent is ethylene glycol-bis(succinimidyl succinate).

12. The method of claim 3 wherein the reagent is disuccinimidyl suberate.

* * * * *